(12) United States Patent
Minetti

(10) Patent No.: US 11,850,169 B2
(45) Date of Patent: Dec. 26, 2023

(54) APPARATUS FOR TRANSFORMING TEETH INTO BONE GRAFT MATERIAL

(71) Applicant: TT TOOTH TRANSFORMER S.R.L., Milan (IT)

(72) Inventor: Elio Minetti, Spiazzo (IT)

(73) Assignee: TT TOOTH TRANSFORMER S.R.L., Milan (IT)

( * ) Notice: Subject to any disclaimer, the term of this patent is extended or adjusted under 35 U.S.C. 154(b) by 667 days.

(21) Appl. No.: 17/053,133

(22) PCT Filed: May 8, 2018

(86) PCT No.: PCT/IB2018/053174
§ 371 (c)(1),
(2) Date: Nov. 5, 2020

(87) PCT Pub. No.: WO2019/215477
PCT Pub. Date: Nov. 14, 2019

(65) Prior Publication Data
US 2021/0236303 A1    Aug. 5, 2021

(51) Int. Cl.
*A61F 2/46* (2006.01)

(52) U.S. Cl.
CPC .... *A61F 2/4644* (2013.01); *A61F 2002/4645* (2013.01); *A61F 2002/4646* (2013.01)

(58) Field of Classification Search
CPC .................................................. A61F 2/4644
See application file for complete search history.

(56) References Cited

U.S. PATENT DOCUMENTS

2018/0214282 A1* 8/2018 Minetti ................ A61C 8/0013

FOREIGN PATENT DOCUMENTS

| EP | 3005977 A1 | 4/2016 |
|---|---|---|
| WO | 0053128 A1 | 9/2000 |
| WO | 2014111925 A1 | 7/2014 |
| WO | 2017017577 A1 | 2/2017 |

OTHER PUBLICATIONS

The International Search Report and Written Opinion, dated Feb. 5, 2019, 8 pages total.

* cited by examiner

*Primary Examiner* — Sameh R Boles
(74) *Attorney, Agent, or Firm* — Vorys, Sater, Seymour and Pease LLP

(57) ABSTRACT

An apparatus for transforming teeth into bone material, which is suitable to treat the teeth by immersion in liquids and includes a reactor device including a contactor, a reaction chamber, an ejection chamber, a cartridge including a plurality of containers for the processing and washing liquids, separated liquid-tight from each other, a fragmentation device suitable to fragment teeth, a guide suitable to detachably connect the cartridge and the fragmentation device to the apparatus, and a movement device suitable to detachably connect at least partially the reactor device and allow it to sequentially withdraw the teeth from the fragmentation device and the liquids from the cartridge.

13 Claims, 4 Drawing Sheets

APPARATUS FOR TRANSFORMING TEETH INTO BONE GRAFT MATERIAL

The present invention relates to an apparatus for transforming teeth into bone graft material of the type specified in the preamble of the first claim.

Procedures and methods are currently known for transforming a tooth or a portion of a tooth into bone material suitable to form the base for supporting a new tooth or for other purposes.

In particular, the tooth is extracted, washed, minced and treated with various liquids. In particular, the treatment takes place with chloroform, methanol, hydrochloric acid and hydrogen peroxide mixtures, for several hours or even days.

The transformed tooth is therefore bone powder with the same DNA as the bone of the patient from whom the tooth was extracted.

The bone thus formed can then be used in the same patient as the base for an implant and for its formation and integration with the bone, for example the jaw into which an artificial tooth is to be fitted.

This process has been known for about twenty years and is described, for example, in Korean patent applications KR-A-20030068957 and KR-A-19980008980 and also in the scientific article entitled "Development of a novel bone grafting material using autogenous teeth" and published in the journal Oral Surg Oral Med Oral Pathol Oral Radiol Endod 2010; 109:496-503. Said process is also disclosed in patent application WO-A-2017/017577.

Said method is very advantageous in that it allows a better integration of the prosthesis, in particular of the dental type, in the bone of the patient and a better healing of the latter.

A number of apparatuses have been realized in order to carry out this process.

However, said apparatuses have major drawbacks.

In fact, the same are very complex and expensive and furthermore do not guarantee patient sterility and do not protect the patient against cross-infection.

Because of their complexity, they are subject to malfunctions.

Lastly, said apparatuses do not allow precise and safe dosage and composition of the treatment liquids and some of the liquids used are also toxic.

In this context, the technical task underlying the present invention is to devise an apparatus for transforming teeth into bone material, which is capable of substantially obviating the above-mentioned drawbacks.

Within the scope of said technical task, a major object of the invention is to obtain an apparatus for transforming teeth into bone material, which is simple, inexpensive and robust.

Another major object of the invention is to provide an apparatus for transforming teeth into bone material, which allows a precise and unequivocal supply of treatment liquids.

The technical task and the specified objects are achieved as claimed in the appended claim 1.

Preferred embodiments are set forth in the dependent claims.

The features and advantages of the invention will be apparent from the detailed description of preferred embodiments of the invention, with reference to the accompanying drawings, in which.

Figure 2:
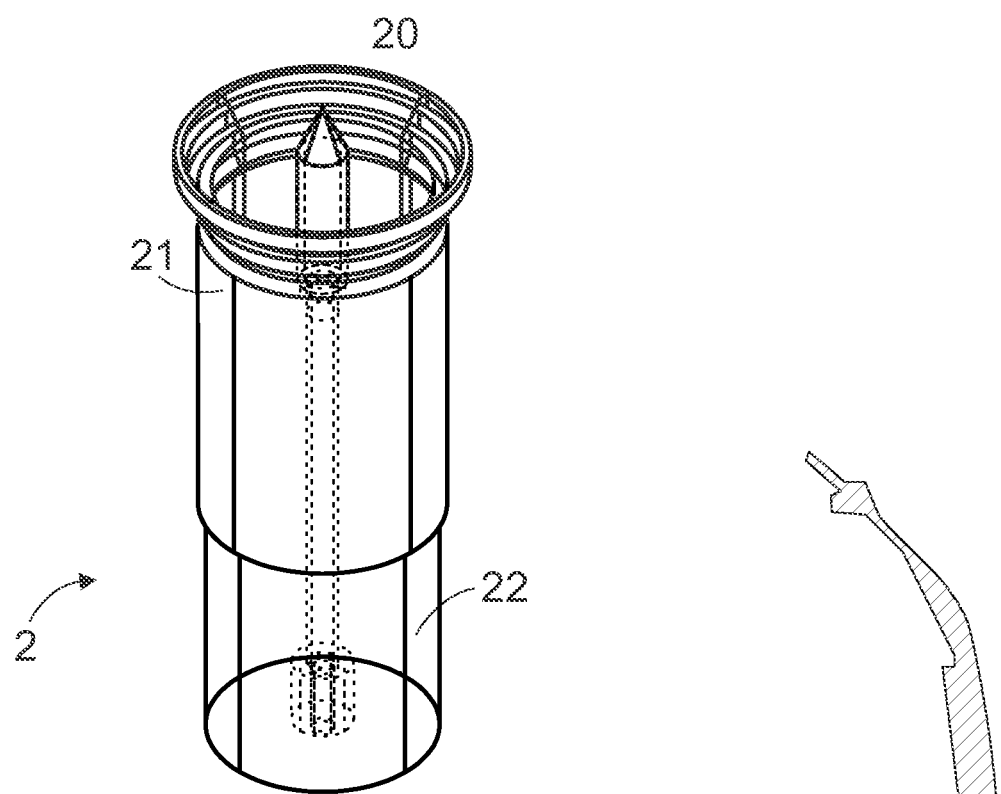
FIG. 2 shows an axonometric view of a first detail of the apparatus for transforming teeth into bone material according to the invention.
Figure 1:
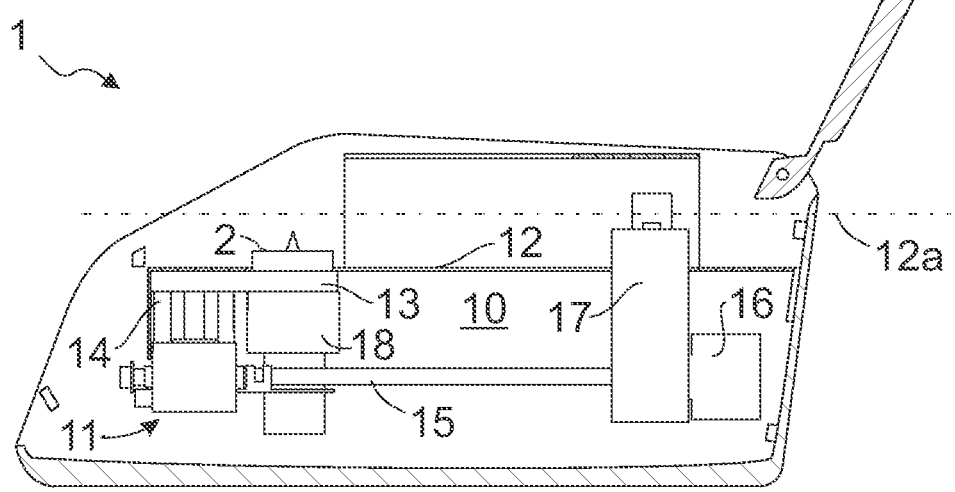
FIG. 1 shows a diagram of the apparatus for transforming teeth into bone material according to the invention.
Figure 3:
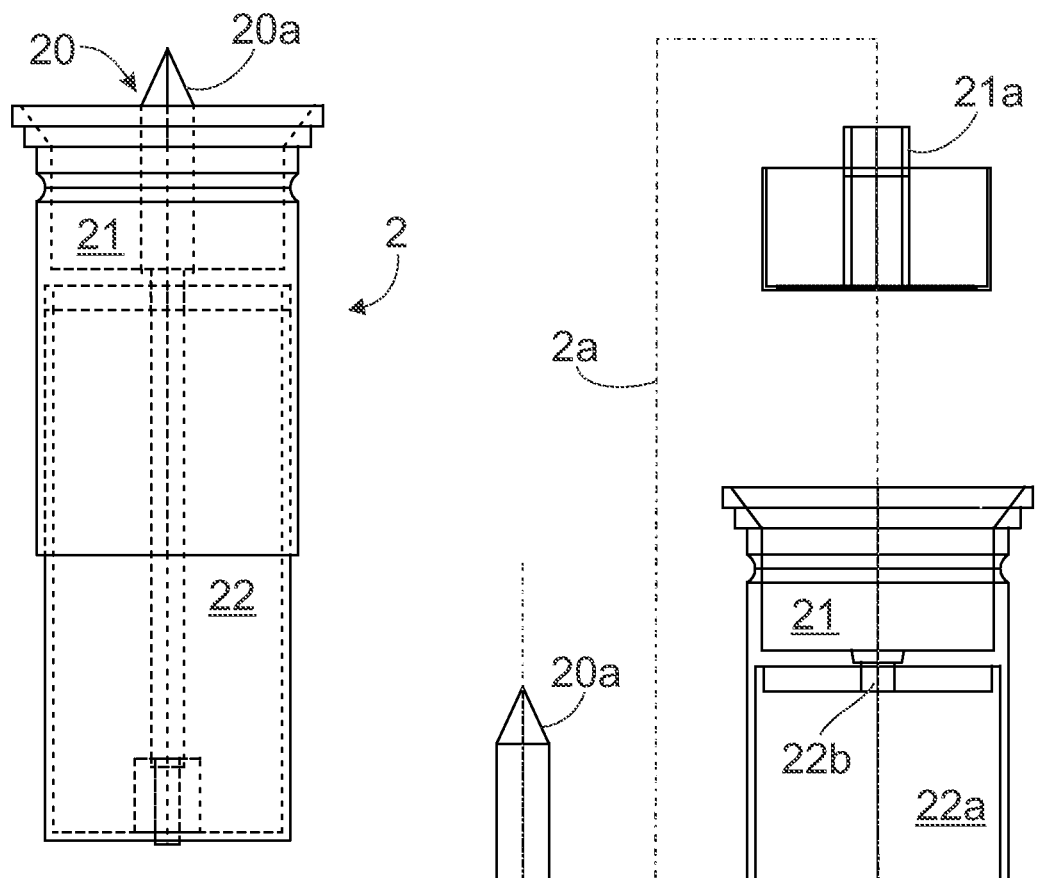
FIG. 3 shows a side view of the first detail of the apparatus for transforming teeth into bone material according to the invention.
Figure 4:
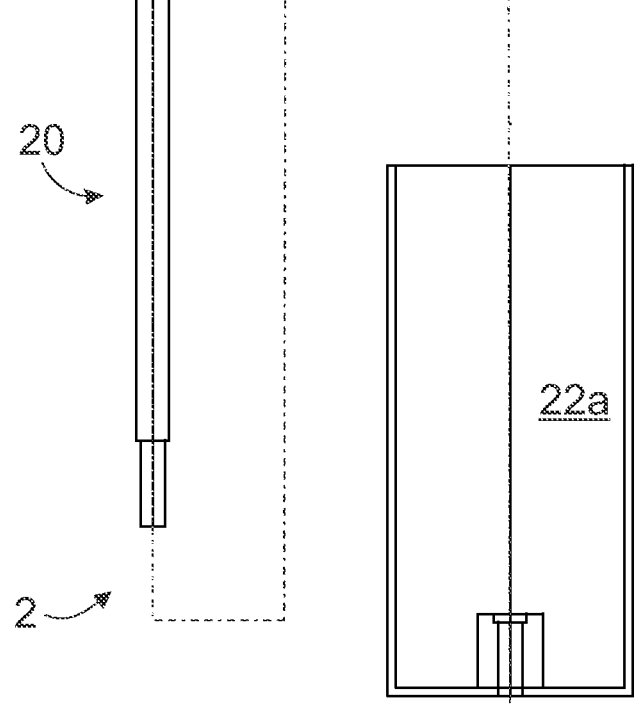
FIG. 4 shows a side exploded view of the first detail of the apparatus for transforming teeth into bone material according to the invention.
Figure 5:
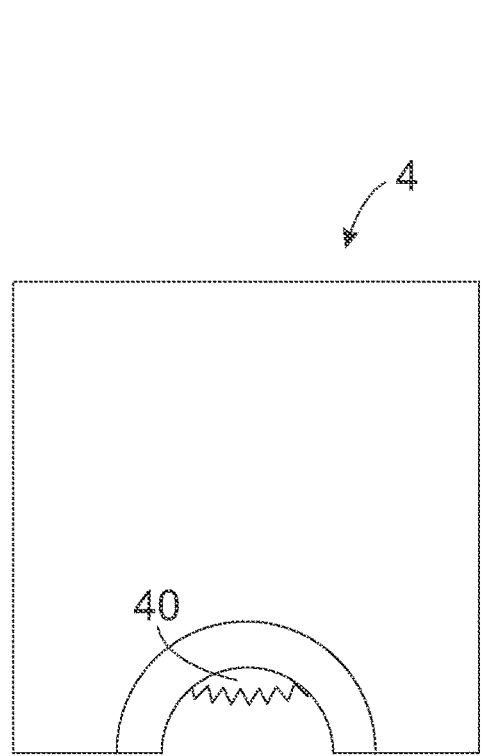
FIG. 5 shows a top view of a second portion of the apparatus for transforming teeth into bone material according to the invention.
Figure 6:
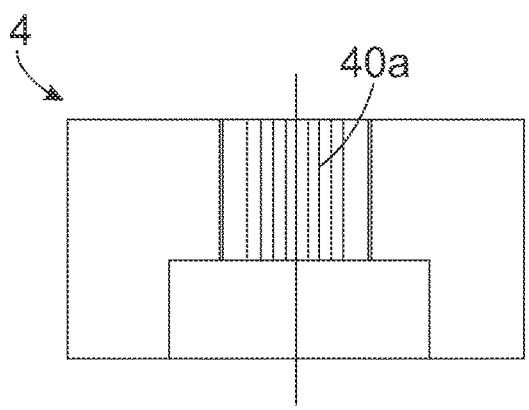
FIG. 6 shows a side view of the second portion of the apparatus for transforming teeth into bone material according to the invention.
Figure 7:
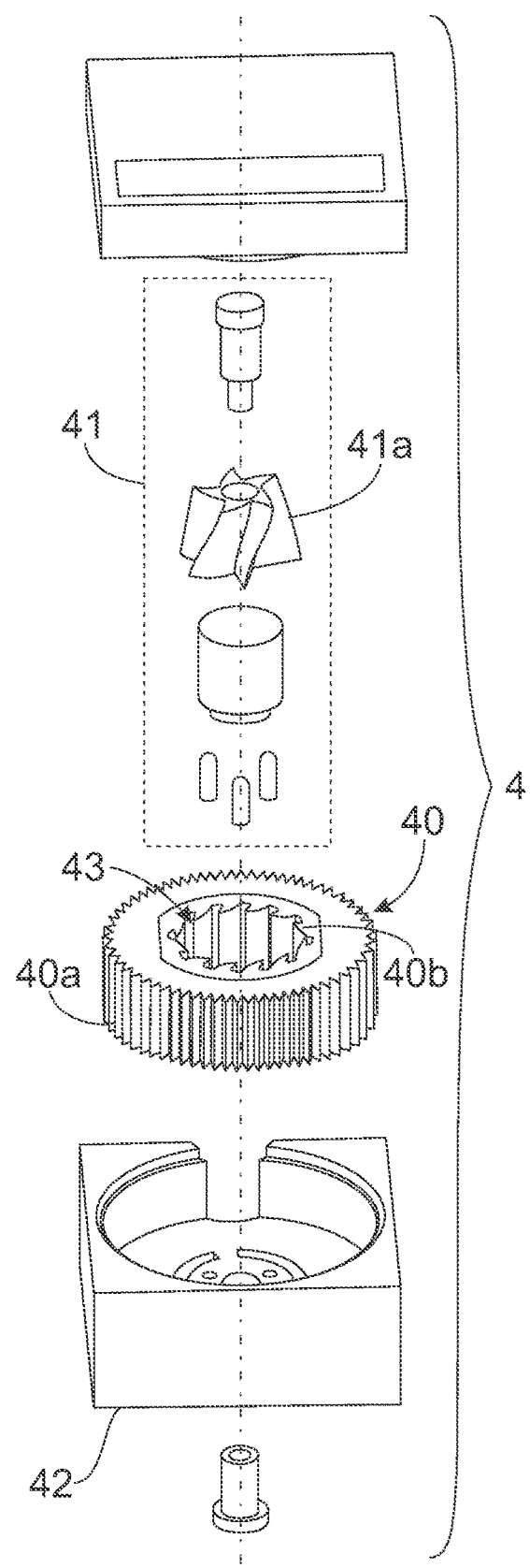
FIG. 7 shows an exploded view of the second portion of the apparatus for transforming teeth into bone material according to the invention.
Figure 8:
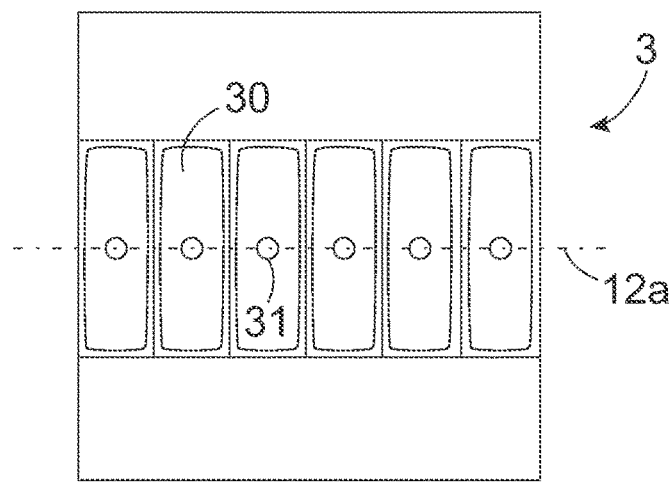
FIG. 8 shows a top view of a third portion of the apparatus for transforming teeth into bone material according to the invention.
Figure 9:
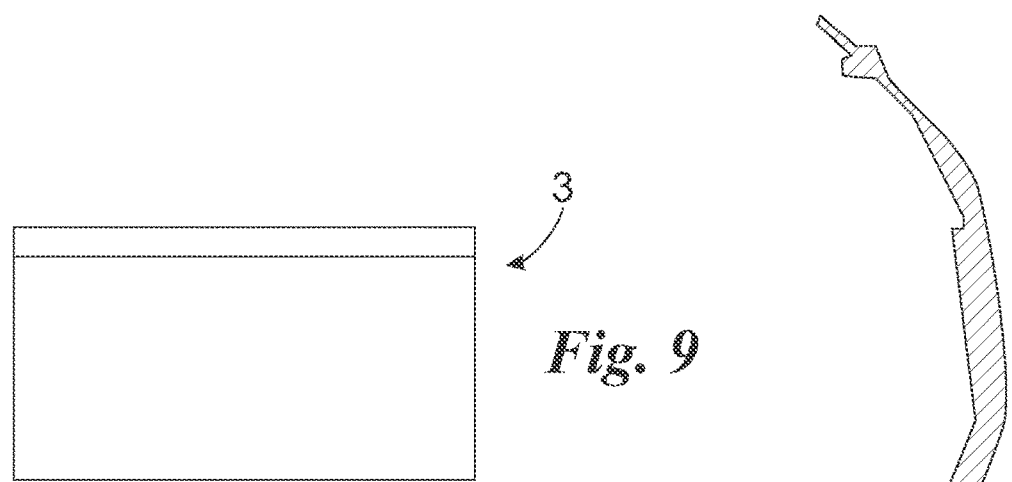
FIG. 9 shows a side view of the third portion of the apparatus for transforming teeth into bone material according to the invention.
Figure 10:
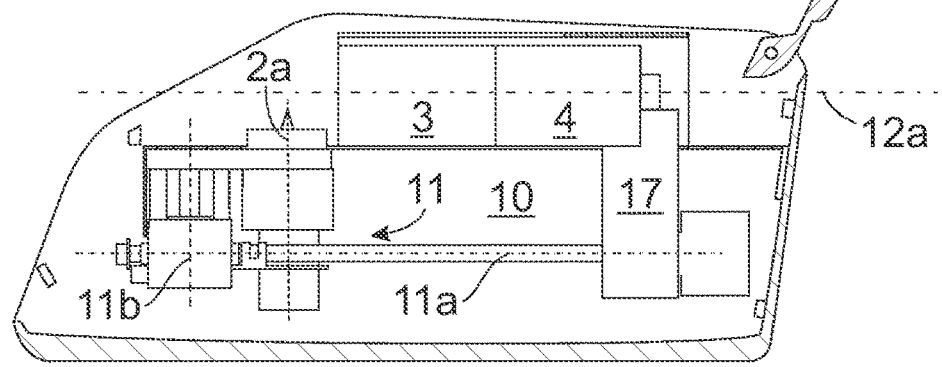
FIG. 10 shows a second diagram of the apparatus for transforming teeth into bone material according to the invention.

With reference to the Figure, the apparatus for transforming teeth into bone graft material according to the invention is indicated as a whole by reference number 1. It acts according to processes and reactions known per se and previously described and is able to transform an autologous human tooth into bone material for supporting a new tooth or for other purposes in the same patient.

Preferably, the apparatus 1 defines a containment volume 10.

This containment volume 10 is, for example, defined by a closed casing comprising at least one portion that can be opened and closed, allowing a user, when necessary, to have free access to the containment volume 10.

Moreover, the containment volume 10 preferably comprises a movement device 11 and a guide 12.

The movement device 11 is preferably a mechanism arranged in the lower portion of the apparatus 1.

The movement device 11 thus defines, for example, a longitudinal axis 11a and a vertical axis 11b perpendicular to the longitudinal axis 11a.

The movement device 11 preferably comprises a support 13, a first movement member 14 and a second movement member 15.

The support 13 preferably includes at least one connection portion that is suitable to allow an object to be coupled to the movement device 11.

In detail, for example, the support 13 comprises at least one circular cross-section ring, the axis of which is arranged parallel to or coinciding with the vertical axis 11b. In this manner, any substantially cylindrical object can be fastened on the support 13, for example by interlocking or by being supported or the like.

The first movement member 14 is at least partially connected to the support 13.

Preferably, the first movement member 14 is suitable to move the support 13 along the vertical axis 11b.

In detail, the first movement member 14 is composed, for example, of one or more pistons connected to a base and suitable to move the support 13 upwards or downwards with respect to the base.

The first movement member 14 can thus be either mechanical, or electromechanical, or electrical, or magnetic and may have linear actuators, as set forth in the example, or cams, gears or the like.

The second movement member 15 is at least partially connected to the first movement member 14, or alternatively, a portion thereof can be integrated into the first movement member 14.

Preferably, the second movement member 15 is suitable to move the first movement member 14, and hence the support 13 along the longitudinal axis 11a.

In detail, the second movement member 15 can also be composed of one or more pistons connected to a base and suitable to move the support 13 to the right or the left with respect to the base.

However, preferably, the second movement member 15 comprises a bar or a rail suitable to allow the support 13 to slide along the longitudinal axis 11a.

The rail can be composed of one or more bars, and the sliding mechanism, for example, is either mechanical, or electrical or the like, as already known in the current state of the art.

In addition, the movement members 14, 15 can be connected to a control member 16.

This control member 16, for example, can consist of an electronic processor suitable to control the movement of the movement members 14, 15.

In particular, the electronic processor can be set so as to allow the support 13 to move along a defined path as a result of an input by a user.

This input, for example, can be supplied by a button located on the casing forming the apparatus 1.

In detail, the control member 16 may comprise an electronic board of the Arduino or Raspberry type, or the like.

The guide 12 is preferably a support arranged at the upper part of the apparatus 1. Preferably, the guide 12 is, in detail, a perforated support suitable to enable one or more objects to slide thereon along a direction 12a parallel to the longitudinal axis 11a. Moreover, the hole is preferably suitable to connect operatively the area above the apparatus 1 with the area housing the movement device 11.

Therefore, the guide 12 is preferably substantially a support suitable to detachably connect one or more removable objects to the apparatus 1.

At least one portion of the guide 12 is preferably engaged by one or more actuators 17.

The actuators 17, for example, consist of a suitably electric rotary engine, more preferably a stepper motor, ending with a connection member, such as for example a gear defining an axis of rotation.

Therefore, the actuators 17 are suitable to transmit motion to at least one component of the apparatus 1.

Briefly, the apparatus 1 comprises a reactor device 2 for carrying out chemical reactions through liquids in particular, a cartridge 3 for containing processing and washing liquids, and a tooth fragmentation device 4 suitable to fragment said teeth. In detail, the cartridge 3 comprises a plurality of containers 30 for processing and washing liquids, separated liquid-tight from each other.

The cartridge 3 is preferably suitable to be housed and moved on the guide 12, and therefore has shapes and dimensions compatible with the guide 12.

The cartridge 3 is preferably a rectangular parallelepiped-shaped casing and the containers 30 are substantially portions, also having a rectangular base, contained inside the cartridge 3. Preferably, there are six to eight containers 30, of which at least three processing ones, in detail acidic solutions, buffer solutions and an alcohol, and at least four washing ones. The containers 30 are suitable to contain, and preferably each contains the necessary and sufficient amount for a single operation.

The containers 30 are preferably separated liquid-tight from each other.

The cartridge 3 further comprises connection means 31 for the connection to the reactor device 2.

The connection means 31 preferably are holes on the bottom of the containers 30. In particular, the connection members 31 are circumferences whose axis is parallel to the vertical axis 11b.

In detail, preferably, the connection members 31 are suitable to connect the internal volume of the containers 30 with the area below the guide 12, and arranged so as to be aligned along the direction 12a when the cartridge 3 is inserted in the guide 12.

In addition, preferably, the liquids in the containers 30 are suitable to flow out of the containers 30 through the connection members 31 by gravity.

Therefore, in non-use conditions, the connection members 31 are covered with a watertight film, which prevents the leakage of liquids included inside the containers 30 through the holes forming the connection members 31.

This film is thus suitable to be removed or torn when the containers 30 are being used.

All the contents of the containers 30 can be released in a single operation, since the liquid itself is already correctly dosed and compounded in the cartridge 3.

Lastly, the cartridge 3 is preferably of the single-use or disposable type.

The reactor device 2 is suitable to treat teeth by immersion in liquids.

In particular, the reactor device 2 is preferably suitable to be attached to the support 13 when in use. Therefore, the reactor device 2 is preferably at least partially removably attached to the apparatus 1 by means of the support 13.

Therefore, the reactor device 2 preferably defines a main axis 2a and consists of a container in one or more pieces, substantially cylindrical in shape, whose axis coincides with the main axis 2a.

Briefly, it also comprises contact means 20 for contacting the cartridge 3, suitable to place the cartridge 3 in mechanical connection and/or fluidic through connection with the reactor device 2, a reaction chamber 21, which is suitable to contain the teeth during the processing and the processing and washing liquids, and an ejection chamber 22 for ejecting the liquids from the reaction chamber 21.

In more detail, the contact means 20 comprise a cutting member 20A, of a known type, such as a sharp point or the like, preferably designed to place the connection members 31 of the cartridge 3 in the operative configuration.

In particular, the cutting member 20a is suitable to pierce the film present on the connection members 31 so as to place the selected container 30 in fluidic through connection with the reactor device 2.

In particular, the piercing preferably takes place when the reactor device 2 is moved in the vertical direction along the vertical axis 11b by the first movement member 14 and when the cartridge 3 and the reactor device 2 are correctly aligned.

In particular, the correct alignment occurs when the main axis 2a is aligned with the centre of one of the holes arranged below a container 30.

The reaction chamber 21 is suitable to contain the teeth, or the powder of the teeth or bone and the liquids during reactions and washes. It is preferably made of metal, more preferably stainless steel, and suitable to be sterilized in an autoclave or disposable. The reaction chamber 21 preferably has a cylindrical shape with a central portion within which said reactions take place. It may also comprise openings for loading the teeth or for inspection.

Preferably, the reaction chamber 21 comprises a basket 21a removably attached to the inside of the reaction chamber 21.

Said basket 21a preferably has a substantially cylindrical shape and includes a liquid-permeable grid at its lower base. Preferably, the basket 21a, just like the reaction chamber, also comprises a base open in the upper portion so as to allow the basket 21a to receive the liquid coming from the containers 30, or other deposited materials, by falling or gravity.

The ejection chamber 22 preferably comprises a drainage tank 22a, which is suitable to contain the liquids after the treatment and preferably releasably constrained to the rest of the device 2. The drainage tank 22a and the reaction chamber 21 are preferably in reciprocal fluidic through connection and separated by a discharge hole 22b.

Preferably, the fluids are transferred from the reaction chamber 22 to the drainage tank 22a by falling through the discharge hole 22b.

The tooth fragmentation device 4 preferably defines a secondary axis 4a.

In addition, it is preferably suitable to fragment said tooth or a piece of tooth into particles of between 0.3 mm and 0.8 mm in diameter.

The fragmentation device 4 is preferably suitable to be housed and moved on the guide 12, and therefore has shapes and dimensions compatible with the guide 12.

It also comprises a partially closed box 42, a mill 40 and a pin 41; in particular, the mill 40 and the pin 41 are housed in said container 42.

The box 42 preferably has a lid and at least one open portion to allow the internal components to come into contact with external elements.

Preferably, the pin 41 is statically arranged inside the box 42 and is centred with respect to the secondary axis 4a.

The pin 41 further comprises an abrasive surface 41a. This abrasive surface 41a includes grooves, for example teeth grooves, suitable to abrade the objects with which it comes into contact.

Preferably, the mill 40 is at least partly exposed to the outside of the closed container and is suitable to rotate around the secondary axis 4a. Furthermore, the mill 40 is preferably oriented so that the axis 4a is parallel to the axis of rotation of the gear arranged on at least one actuator 17.

Therefore, the pin 41 and the mill 40 define therebetween at least one volume 43. This volume 43 is preferably suitable to house therein the teeth to be fragmented. The teeth may be inserted inside the volume when the lid of the box 42 is removed. Preferably, the mill 40 consists of a ring comprising an outer belt 40a and an inner belt 40b.

In particular, the outer belt 40a is preferably suitable to contact the gear of at least one actuator 17 and includes, for example, grooves, for example of the type present on common gears, compatible with the gear of at least one actuator 17, so as to transmit the rotary motion of at least the actuator 17 to the mill 40.

The inner belt 40b, on the other hand, preferably comprises an abrasive surface.

This abrasive surface comprises teeth suitable to break the teeth housed within the volume 43.

In particular, the teeth are fragmented owing to the relative motion between the abrasive surfaces of the pin 41 and of the inner belt 40b.

Lastly, the box 42 comprises a hole located at the bottom thereof and communicating with the outside, suitable to allow tooth debris or fragments to escape from it by gravity.

Preferably, this hole is aligned with the secondary axis 4a and arranged below the volume 43.

In particular, the tooth fragments are preferably suitable to be conveyed to the reactor device 2 when the latter is correctly positioned below the box 42, and in particular, the fragments are suitable to be deposited in the reaction chamber 21, and more in detail, in the basket 21a.

The apparatus 1 may finally comprise auxiliary components 18.

Part of the auxiliary components 18 can be arranged in the area of the reaction chamber 21, in particular where it is coupled to the support 13, are preferably heating means, ultrasonic vibrating means and UV light emitters.

These heating means, ultrasonic vibrating means and UV light emitters are designed to interact with the reaction chamber 21 and the liquids contained therein, preferably of the electric type and preferably elastically connectable to and separable from the reaction chamber 21.

Another auxiliary component 18 can comprise means (not shown) for reading the position of the cartridge 3 or of the fragmentation device 4, which interact with the control member 16 and with means for indicating the position of the cartridge 3, are suitable to allow the device 2 to read the position of the cartridge 3, in particular of the tanks 30 with respect to the device 2, and more in detail to the contact means 20 or fragmentation means 4.

The operation of the apparatus 1 for transforming teeth into bone material, previously described in structural terms, is as follows.

A tooth is extracted from the patient.

The same tooth is inserted in the box 42 of the fragmentation device 4 where it is fragmented into particles of between 0.3 mm and 0.8 mm in diameter by the mill 40 rotating about the pin 41.

Before the tooth is fragmented, the control member 16 positions the reactor device beneath the hole of the box 42.

The fragments are then deposited in the reaction chamber 21 of the device 2.

At the same time, a cartridge 3 is positioned inside the guide 12.

The reactor device 2 is then positioned so that the contact means 20 are aligned with the connection means 31.

In particular, the means for reading the position of the cartridge 3 read the position of the containers 30 of the cartridge 3, and the movement means 14, 15 of the cartridge 3 position a specific tank above the contact means 20. The first movement means 14 move the contact means 20, which pierce the connection means 31 of the selected container 30.

The liquids contained in the selected container 30 fall into the reaction chamber 21 and come into contact with the basket 21a, triggering a specific reaction or washing with the tooth fragments.

When the treatment with the specific liquid, which is carried out in a predetermined time interval, is finished, the device 2 can be removed from the support 13, and the basket 21a can be removed so as to remove the fragments of teeth from the device 2.

A new reactor device 2, and preferably a new cartridge 3 can then be arranged in the apparatus so as to repeat the process on one or more other teeth.

Preferably, washing cycles are alternated with washing and reaction liquids, which are preferably carried out with HCl, $H_2O_2$ and an alcohol for well-known periods of time.

In particular, six liquids are preferably used for six different reactions.

The fragmentation device 4 is preferably sterilized in an autoclave before being used again.

The apparatus 1 for transforming teeth into bone material according to the invention achieves important advantages.

In fact, the apparatus 1 is very simple, inexpensive and robust.

Moreover, the use of the sterile, pre-loaded and disposable cartridge 30 allows precise dosing and a correct composition of the washing and reaction liquids.

The invention is susceptible of variations falling within the scope of the inventive concept as defined by the claims.

In this context, all details are replaceable by equivalent elements, and the materials, shapes and dimensions may be any materials, shapes and dimensions.

The invention claimed is:

1. An apparatus for transforming teeth into bone graft material suitable to treat said teeth by immersion in liquids, and comprising:
    a reactor device including contact means, a reaction chamber and an ejection chamber,
    a cartridge including a plurality of containers for said processing and washing liquids, separated liquid-tight from each other,
    a fragmentation device suitable to fragment said teeth,
    a guide suitable to detachably connect said cartridge and said fragmentation device to said apparatus, and
    a movement device suitable to detachably connect at least partially said reactor device to said apparatus and allow said reactor device to sequentially withdraw said teeth from said fragmentation device and said processing and washing liquids from said cartridge.

2. The apparatus according to claim 1, wherein said containers comprise connection means arranged on the bottom of said containers and substantially consisting of holes blocked by a film and configured to allow said liquids to escape from said cartridge by gravity when said film is torn.

3. The apparatus according to claim 2, wherein said contact means comprise a cutting member configured to pierce said film of said connection means to place at least one of said containers in fluidic through connection with said reactor device.

4. The apparatus according to claim 3, wherein said movement means define a longitudinal axis, a vertical axis perpendicular to said longitudinal axis and comprise a support, a first movement member and a second movement member, said support being configured to detachably connect said reactor device, said first movement member being configured to move said support along said vertical axis, and said second movement member being configured to move said support along said longitudinal axis.

5. The apparatus according to claim 4, wherein said fragmentation means define a secondary axis and comprise a box, a mill and a pin, said box comprising at least partially said mill and said pin, said mill being configured to rotate about said secondary axis, said pin being statically aligned with said secondary axis and said mill, and said pin defining at least one volume configured to house one or more of said teeth therein.

6. The apparatus according to claim 1, wherein said contact means comprise a cutting member configured to pierce said film of said connection means to place at least one of said containers in fluidic through connection with said reactor device.

7. The apparatus according to claim 1, wherein said movement means define a longitudinal axis, a vertical axis perpendicular to said longitudinal axis and comprise a support, a first movement member and a second movement member, said support being configured to detachably connect said reactor device, said first movement member being configured to move said support along said vertical axis, and said second movement member being configured to move said support along said longitudinal axis.

8. The apparatus according to claim 1, wherein said fragmentation means define a secondary axis and comprise a box, a mill and a pin, said box comprising at least partially said mill and said pin, said mill being configured to rotate about said secondary axis, said pin being statically aligned with said secondary axis and said mill, and said pin defining at least one volume configured to house one or more of said teeth therein.

9. The apparatus according to claim 1, wherein said box comprises a lid configured to allow said teeth to be placed inside the box and at least one hole aligned with said secondary axis on the bottom of said box and configured to allow fragments of said teeth to come out of said box by falling or gravity.

10. The apparatus according to claim 1, wherein said pin comprises an abrasive surface, said mill comprises an outer belt including grooves configured to interact with external gears, and an inner belt including an abrasive surface, said teeth being fragmented due to the relative motion between said abrasive surface and said inner belt.

11. The apparatus according to claim 1, comprising a control member, at least one actuator and auxiliary means, said auxiliary means comprising means for reading the relative position between said cartridge and said reactor device or said fragmentation device and said reactor device, said actuator being a rotary engine comprising a gear configured to transmit a rotary motion to said mill by means of said outer belt, and said control member being an electronic processor configured to control the movement of the movement members by interacting with said auxiliary means.

12. The apparatus according to claim 1, wherein said cartridge and said reactor device are of the disposable type.

13. The apparatus according to claim 1, wherein the tooth fragmentation device is configured to fragment a tooth or a piece of tooth into particles of between 0.3 mm and 0.8 mm in diameter.

* * * * *